(12) United States Patent
Baltimore

(10) Patent No.: US 8,313,643 B1
(45) Date of Patent: Nov. 20, 2012

(54) SYSTEM AND METHOD FOR ANALYZING A BIOLOGICAL SAMPLE

(76) Inventor: David Baltimore, Newtown, CT (US)

( * ) Notice: Subject to any disclaimer, the term of this patent is extended or adjusted under 35 U.S.C. 154(b) by 56 days.

(21) Appl. No.: 12/589,234

(22) Filed: Oct. 20, 2009

Related U.S. Application Data

(60) Provisional application No. 61/196,659, filed on Oct. 20, 2008.

(51) Int. Cl.
*G01N 37/00* (2006.01)
(52) U.S. Cl. .......... 210/180; 210/175; 436/164; 436/73; 436/807; 422/50; 422/63; 422/68.1
(58) Field of Classification Search .................. 210/180, 210/175; 422/50, 63, 68.1, 99; 436/164, 436/73, 807; 435/283.1, 6, 7.1, 4, 287.1
See application file for complete search history.

(56) References Cited

U.S. PATENT DOCUMENTS 6,444,461 B1 * 9/2002 Knapp et al. ............... 435/283.1

* cited by examiner

*Primary Examiner* — Christine T Mui
(74) *Attorney, Agent, or Firm* — Steven M. McHugh

(57) ABSTRACT

A system and method for analyzing a biological substance, the device comprising: a specimen input device; at least one pumping device in flow communication with a chemical reservoir and said specimen input device; and at least one flow cell in flow communication with said at least one pumping device via at least one flow valve, wherein said at least one flow cell is configured to contain said specimen and includes a sensing device configured to sense at least one characteristic of said specimen.

9 Claims, 21 Drawing Sheets

Optimal

If Saliva pH is between 6.5 and 6.75 inclusive and Urine pH is between 6.5 and 6.8 inclusive.

Zone 1 – early alkaline reserve use

If ((Urine pH >= 6.5) and (Saliva pH > 6.5)
slope = 3.4675
estimated position = -(21 *(10 ^ (( saliva pH – 6.76) / slope)))

Zone 2 – late alkaline reserve use

If ((Urine pH < 6.5) and (Saliva pH > 6.5)
slope = =7.4775
estimated position = -(41 *(10 ^ (( saliva pH – 7.72) / slope)))

Zone 3 – early alkaline reserve loss

If ((Urine pH >= 6.5) and (Saliva pH < 6.5)
slope = =9.4561
estimated position = -(61 *(10 ^ (( saliva pH – 6.49) / slope)))

Zone 4 – late state alkaline reserve loss

If ((Urine pH > 6.5) and (Saliva pH < 6.5)
slope = =9.5252
estimated position = -(81 *(10 ^ (( saliva pH – 5.39) / slope)))

Figure 8

Oxidative Stress rH2 is a modified Nernst equation that factors pH and temperature into the reading of ORP (Oxidation Reductions Potential)

If Saliva rH2 >= 18.5 It's a positive going value
    Value is "gauged" by evaluating it on a percentage from a low value of 18.5 to a high value of 30

If Saliva rH2 < 18.5 It's a negative going value
    Value is "gauged" by evaluating it on a percentage from a low value of 18.5 to a high value of 14

Separately: If the Urine rH2 drops below 18 another marker is noted for an Electron Transport Problem.

Optimal is 18-19

Figure 9

ELECTROLYTES

Electrolytes are evaluated by the resistivity of Saliva

If Saliva r>= 220

The value is gauged by percentage from a low of 220 to a high of 400

Optimal is 180-220

Figure 10

Carbohydrate Metabolism

Carbohydrate metabolism is measured by the refractometer

An ideal reading is 1.3 to 1.9

The carb number is gauged positive going it the number is >= 1.5 it is gauged between a low of 1.5 and a high of 13

If the carb number is below 1.5 then it is negative going and it is gauged between a low of 1.5 and a high of 0

Figure 11

PROTEIN METABOLISM

Protein intake is measured in parts per million (ppm) of the ION Nitrate Nitrogen Protein metabolism measurement is then made more "granular" by the following equation

```
Function ppm to RM (ppm, measure type)
DIM Nitrate as Integer
DIM Y as Integer
DIM slope As Single If measuretype = "N" or Nitrate number
    If ppm < 1000 Then
        ppmtoRM = 2
        Exit Function
    End If
    If ppm > 17500 Then
        ppmtoRM = 14
        Exit Function
    End If
    If ppm > 3179 Then
        ppm = 3180
    End If
    ppmtoRM = 4 * 10 ^ ((ppm=3179)/27000)
Else
```

Figure 12

PROTEIN METABOLISM

The following is for the Ammonium number

If ppm < 10 Then
    ppmtoRM = 1
    Exit Function
End If

If ppm > 595 Then
    ppmtoRM = 12
    Exit Function
End If

If ppm = 200 Then
    ppm = 201
End If
ppmtoRM = 4 * 10 ^ ((ppm - 200)/852)
End If The Nitrate and Ammonium numbers are added together for a Total Urea number. That number is then gauged positive or negative going in the following equation.

Optimal is: Total Urea = 6 to 7

If Total Urea is >= 6
        Protein metabolism is gauged by percentage with a low of 6 and a high of 30
    If Total Urea is < 6
        Protein metabolism is gauged with a low of 6 and a high of 1

Figure 13

Cell Respiration

Cellular Respiration is based on Saliva pH

Optimal is centered on 6.4 pH

If Saliva pH >= 6.4
    Saliva pH is gauged on a percentage with a low value of 6.4 and a high value of 7.7

If Saliva pH < 6.4
    Saliva pH is gauged on a percentage with a low value of 6.4 and a high value of 4.8

Figure 14

HYDRATION

Hydration is based on the refractometry of the Urine and it's mathematically converted into Specific Gravity or SG SG =(1.000019 = (0.003865613 * Carb number) + (0.00001296425 * Carb number) + (0.000000005701128 * Carb number)

Hydration is gauged by percentage from a low of 1.003 to a high of 1.05

Figure 15

Liver Stress / Toxicity

Liver Stress and systemic toxicity are measured by 3 factors

Nitrate Nitrogen, Ammonium Nitrogen and Saliva pH

Liver Stress / Toxicity = Ammonium + Nitrate + ((Saliva pH − 6.4) * 6.4)

If Liver Stress / Toxicity >= 7
    Liver Stress / Toxicity is gauged by percentage with a low value of 7 and a high value of 30

If Liver Stress / Toxicity < 7
    Liver Stress / Toxicity is gauged by percentage with a low value of 6 and a high value of 0

Optimal is 6-7

Figure 16

Kidney Stress

Kidney Stress is measured by Urine conductivity

Optimal is 6-7

Kidney Stress is gauged by percentage with a low value of 6.5 to a high value of 30

Figure 17

Adrenal Stress

Adrenal Stress is measured by Urine resistivity

Adrenal Stress is measured by percentage with a low value of 30 and a high value of 700

Figure 18

Anabolic / Catabolic

Anabolic / Catabolic values is currently measured by Urine pH
6.6 pH is the value of dead center or ideal value.

The degree of Anabolism value is determined by percentage with a low value of 6.6 and a high value of 7.7

The degree of Catabolism value is determined by percentage with a low value of 6.6 and a high value of 4

Inflammation

Inflammation is evaluated by Saliva rH2, Nitrate and Urine Conductivity

Each factor is weighed on a percentage scale:

Saliva rH2 is evaluated on a percentage scale with a low of 18.5 and a high of 30

Nitrate is evaluated on a percentage scale with a low of 7 and a high of 30

Urine Conductivity is evaluated on a percentage scale with a low of 6.5 and a high of 30

If all three markers are >= 80% then Orange range

If two are >= 80% then High Yellow range
If one is >= 80% then Low Yellow range

Otherwise Green range

ION Calibration
| The 100 ppm solution is loaded in the ION electrodes and reference area twice. |  | The values are read by the electronic and collected by the computer program |  | The 1000 ppm solution is loaded in the ION electrodes and reference area twice. |  | The values are read by the electronics and collected by the computer program |
Figure 24

Refractometer Calibration
| Distilled water is flushed down the line to clear any residual solutions. Then Distilled water is parked in the refractometer |
|---|
| The Refractometer calibrates to distilled water |
|---|
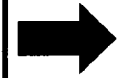
| The distilled water is vented out. |
|---|
Figure 25

SYSTEM AND METHOD FOR ANALYZING A BIOLOGICAL SAMPLE

CROSS REFERENCE TO RELATED APPLICATIONS

This application claims the benefit of U.S. Provisional Patent Application No. 61/196,659, filed Oct. 20, 2008 and entitled "A System and Method for Analyzing a Biological Sample" the contents of which are incorporated herein by reference in its entirety.

FIELD OF THE INVENTION

This invention relates generally to analyzing a biological sample and more particularly to a system and method for analyzing a Bio-Cellular sample.

BACKGROUND OF THE INVENTION

Bio-Cellular analysis is well known and is used in the health/nutrition industry to examine key health indicators that can provide an in-depth view into the overall health of a person or animal. Some of these indicators include pH levels, ORP (oxidation-reduction potential) and conductivity/resistivity of bodily fluids (e.g. Saliva, Urine), as well as Nitrate Nitrogen (Urine), Ammonium Nitrogen (Urine) and refractometry (Urine). Since the ultimate goal of preventive medicine is to optimize homeostasis, Bio-Cellular analysis serves as a sensitive and invaluable way to monitor the optimization progress. Analysis of these key health indicators can help the health care professional assess the condition of the patient and determine/address any underlying causes of any health issues that may be present. For example, based upon the results of the Bio-Cellular analysis, the health care professional may make recommendations or changes to a patient's therapy in order to address imbalances that may have shown up in their Bio-Cellular Analysis test. Another example would be that this information can be used to recommend lifestyle and nutrition changes which would help the patient restore and maintain the vitality of the body. This may be accomplished with the use of nutritional supplements, as well as attention to lifestyle changes, diet, the amount of exercise the patient is getting, proper breathing, and the stress in their life. All of these things greatly affect the terrain of the body, and its ability to keep homeostasis.

Once the results of the Bio-Cellular analysis have been obtained, they are typically compared with a set of guideline or optimum values that are used to determine which indicators are unstable. This will guide the health care professional in his/her recommendations. For example, consider the pH (Potential of Hydrogen) level of a bodily fluid. The pH level is a measurement of the acidity or alkalinity of a solution or bodily fluid, which is dependent upon the number of hydrogen ions present in the solution or bodily fluid (acidic solutions typically have an acidity level between 0 and 6.99, while alkaline solutions typically have an alkalinity between 7.01 and 14.00). Solutions which measure at 7.00, water for example, are considered to be neither acidic nor alkaline and are thus neutral. For venous blood, the pH level is reflective of three factors: 1) respiratory rate; 2) tissue oxygen absorption; and 3) how effective the tissue is using the oxygen to generate energy as well as maintaining good bone density and enzyme and hormone utilization. Respiratory rate is affected because chronic stress combined with improper breathing results in chronic respiratory alkalosis. When tissue oxygen absorption is poor, a higher percentage of oxygen remains in the venous blood resulting in an increase of the pH level of the venous blood. And when tissue is not effectively using oxygen to generate energy, the production of carbon dioxide decreases which lowers the hydrogen concentration in the blood thus raising the pH level of the venous blood.

Unfortunately, current methods for isolating and analyzing these indicators involves conducting multiple individual tests on several fluid samples, resulting in an inefficient process which is both time consuming and expensive. Current methods and systems do not use a synergistic approach to measure and evaluate across the markers to a new conclusion of therapy.

SUMMARY OF THE INVENTION

A system for analyzing a biological substance, the device comprising: a specimen input device; at least one pumping device in flow communication with a chemical reservoir and said specimen input device; and at least one flow cell in flow communication with said at least one pumping device via at least one flow valve, wherein said at least one flow cell is configured to contain said specimen and includes a sensing device configured to sense at least one characteristic of said specimen.

A method for analyzing a biological sample using an analyzing device, wherein the analyzing device includes a specimen input device, at least one pumping device in flow communication with a chemical reservoir and a specimen input device and at least one flow cell in flow communication with the at least one pumping device via at least one flow valve, wherein the at least one flow cell is configured to contain the specimen and includes a sensing device configured to sense at least one characteristic of the specimen, the method comprising: introducing a specimen to be analyzed into the specimen input device; operating the analyzing device to cause the specimen within the specimen input device to flow to the flow cell, such that the specimen is contained within a flow cell cavity; sensing at least one characteristic of the specimen contained within the flow cell cavity; flushing the specimen contained with the flow cell cavity into a waste container; and cleaning the analyzing device by causing a cleaning fluid to flow through the analyzing device into the waste container.

A computer-readable storage medium encoded with machine-readable computer program code, the program code including instructions for causing a controller to implement a method for analyzing a biological sample using an analyzing device, wherein the analyzing device includes a specimen input device, at least one pumping device in flow communication with a chemical reservoir and a specimen input device and at least one flow cell in flow communication with the at least one pumping device via at least one flow valve, wherein the at least one flow cell is configured to contain the specimen and includes a sensing device configured to sense at least one characteristic of the specimen, the method comprising: introducing a specimen to be analyzed into the specimen input device; operating the analyzing device to cause the specimen within the specimen input device to flow to the flow cell, such that the specimen is contained within a flow cell cavity; sensing at least one characteristic of the specimen contained within the flow cell cavity; flushing the specimen contained with the flow cell cavity into a waste container; and cleaning the analyzing device by causing a cleaning fluid to flow through the analyzing device into the waste container.

BRIEF DESCRIPTION OF THE DRAWINGS

The foregoing and other features and advantages of the present invention will be more fully understood from the following detailed description of illustrative embodiments, taken in conjunction with the accompanying drawings in which like elements are numbered alike:

FIG. 8 is block diagram illustrating one embodiment of how to determine acid/alkaline balance or buffer depletion in accordance with the present invention.

FIG. 9 is a block diagram illustrating one embodiment of how to determine oxidative stress in accordance with the present invention.

FIG. 10 is block diagram illustrating one embodiment of how to evaluate electrolytes in accordance with the present invention.

FIG. 11 is a block diagram illustrating one embodiment of how to measure carbohydrate metabolism in accordance with the present invention.

FIG. 12 is a block diagram illustrating how protein intake may be measured of the ION Nitrate Nitrogen and the protein metabolism in accordance with the present invention.

FIG. 13 is a block diagram illustrating how protein intake may be measured of the ION Nitrate Nitrogen and the protein metabolism in accordance with the present invention.

FIG. 14 is a block diagram illustrating one embodiment of how cell respiration is determined in accordance with the invention.

FIG. 15 is a block diagram illustrating one embodiment of how hydration is determined in accordance with the invention.

FIG. 16 is a block diagram illustrating one embodiment of how to determine liver stress/toxicity in accordance with the invention.

FIG. 17 is a block diagram illustrating one embodiment of how to determine kidney stress in accordance with the invention.

FIG. 18 is a block diagram illustrating one embodiment of how to determine adrenal stress in accordance with the invention.

FIG. 19 is a block diagram illustrating one embodiment of how to determine anabolic/catabolic values in accordance with the invention.

FIG. 20 is a block diagram illustrating one embodiment of how to determine inflammation in accordance with the invention.

FIG. 24 is a general block diagram illustrating one embodiment of ION calibration in accordance with the invention.

FIG. 25 is a general block diagram illustrating one embodiment of Refractometer calibration in accordance with the invention.

DETAILED DESCRIPTION OF THE INVENTION

In accordance with the present invention, an analyzer is disclosed which measures several characteristics of a sample, such as blood, urine, saliva, etc. These characteristics include, but are not limited to, ions (such as pH (percentage of hydrogen), Nitrate Nitrogen, Ammonium Nitrogen, Chloride, Nitrite, Iodide), Redox (oxidation/reduction potential), conductivity/resistivity, refractometry and surface tension. It should be appreciated that when combined, the tests performed add up to a powerful diagnostic instrument capable of looking at the metabolic efficiency of the whole human body at a cellular level. One analogy is that of a car dynamometer or tune up meter which measures Spark, Oxygen, Fuel, Torque and Exhaust. By themselves each only gives part of the picture on a pass/fail basis. However, when combined the dynamic opens up the efficiency of the engine itself and opens up a method of tuning the engine to the highest order of efficiency. Each value is related to the overall power/performance of the engine, the overall input of fuel, air and spark to the cleanness of the exhaust and greatest power and speed to the wheels. The same concept can be applied to "tuning" a human being at a cellular level. The smallest common denominator in the body is the cell. The human body is made up of organs, each with having its own set of functions, but common to all organs is the cell. If you think of the cell as the engine of the body, we are looking at the factors that affect the performance of the body at a cellular level. The invention measures various inputs and outputs of the body. When triangulated and optimized, the core physiologic health is optimized. As with automotive measurements, each measurement alone is only a pass/fail measurement, but when combined into a cohesive analysis, the overall, "wellness", performance and vitality of the person can be optimized to a fine degree. In essence, the invention is a unique and synergistic approach at examining multiple parameters providing a cumulative measurement across the parameters.

Figure 1:
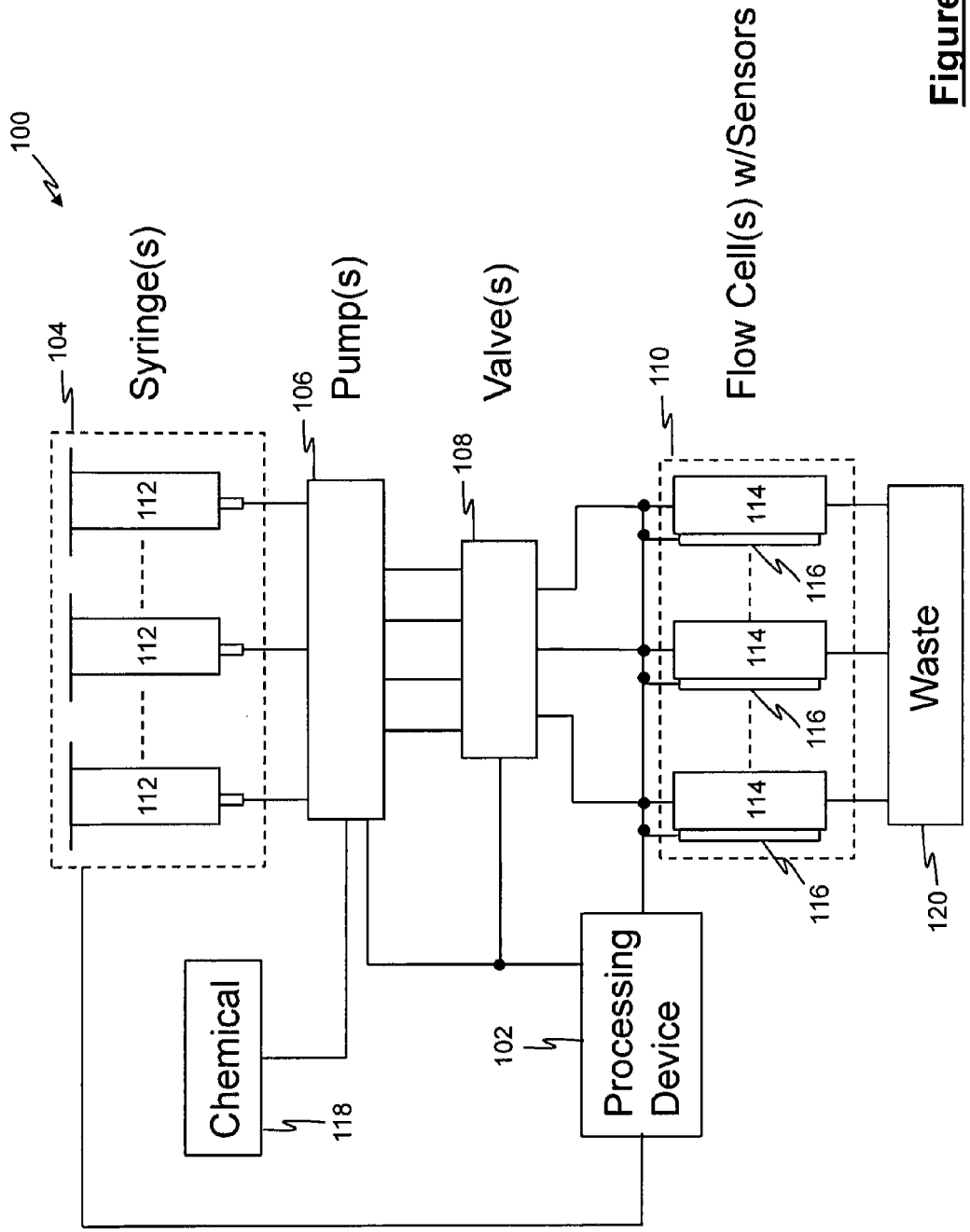
FIG. 1 is schematic block diagram of a system for analyzing a biological sample in accordance with the present invention.

Referring to FIG. 1, a schematic block diagram illustrating a system 100 for analyzing at least one biological sample is shown, in accordance with the present invention. The system 100 includes a processing device 102, at least one specimen input device 104, a pumping device 106, a flow valve 108 and at least one flow cell 110, wherein at least one specimen input device 104 may include one or more specimen input devices and the at least one flow cell 110 may include one or more flow cells. It should be appreciated each of the specimen input devices 104 are operably connected with each of the flow cells 110 via the at least one pumping device 106 and the at least one flow valve 108 to allow for the controlled flow of specimen between the specimen input devices 104 and the flow cells 110. Accordingly, the specimen can be controllably directed to flow between any of the specimen input devices 104 and any of the flow cells 110.

It should be appreciated that each of the specimen input devices 104 defines a specimen input cavity 112 for containing a specimen to be analyzed and each of the flow cells 110 define a flow cell cavity 114 for containing at least a portion of the specimen to be analyzed. The system 100 also includes a plurality of sensors 116 associated with the flow cells 110 for analyzing at least one characteristic of the specimen contained with each or one of the flow cell cavities 114. System 100 further includes a chemical reservoir 118 which is operably connected with each of the flow cells 110 via the at least one pumping device 106 and the at least one flow valve 108 to allow for the controlled flow of chemical between the chemical reservoir 118 and the flow cells 110. It is contemplated that the chemical reservoir may include any type of substance suitable to the desired end purpose. Accordingly, the chemical can be controllably directed to flow through any of the valves of at least one flow valve 108 into any of the flow cells 110. Moreover, each of the flow cells 110 are in flow communication with a waste container 120 for disposal of the chemicals and/or specimen.

The processing device 102 is operably associated with at least one of the specimen input devices 104, the pumping device 106, the flow valves 108, the flow cells 110 and the plurality of sensors 116. This allows the processing device 102 to control and/or transfer data between the at least one of the specimen input devices 104, the pumping device 106, the flow valves 108, the flow cells 110 and the plurality of sensors 116.

Figure 2:
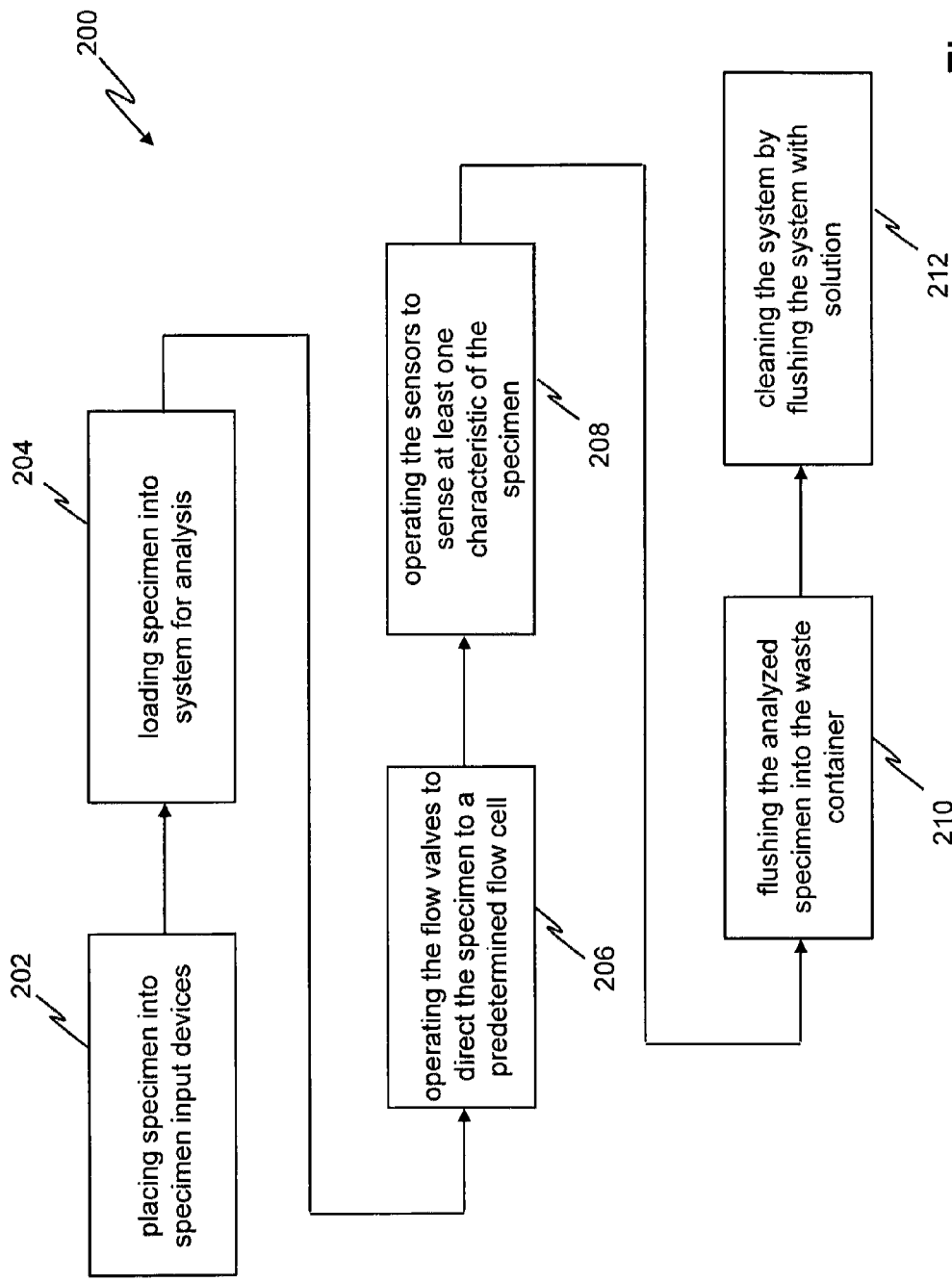
FIG. 2 is a block diagram illustrating a method for implementing the system of FIG. 1, in accordance with the present invention.
Figure 3:
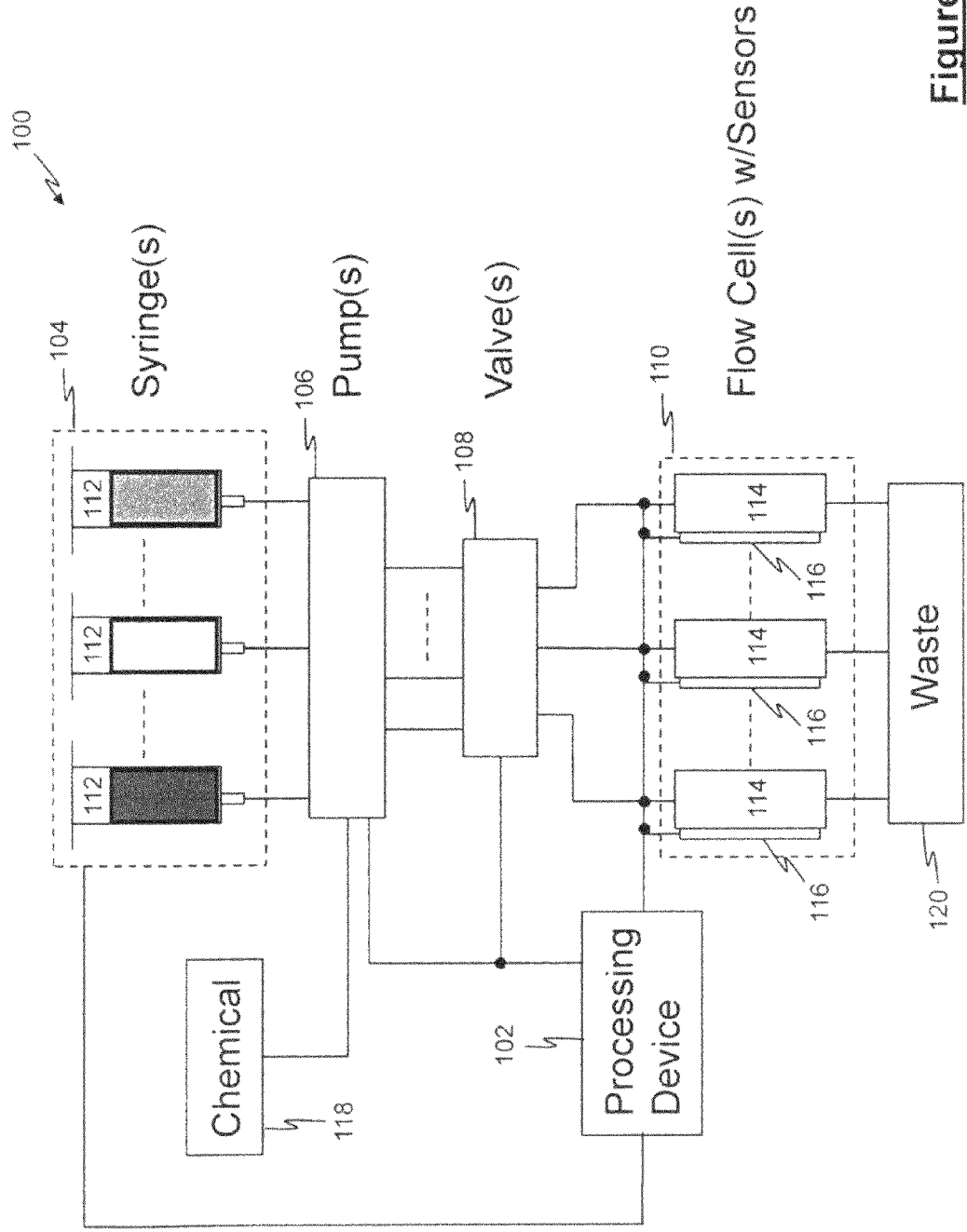
FIG. 3 is a schematic block diagram of the system in FIG. 1 illustrating one embodiment of an operational flow of specimen through the system.
Figure 4:
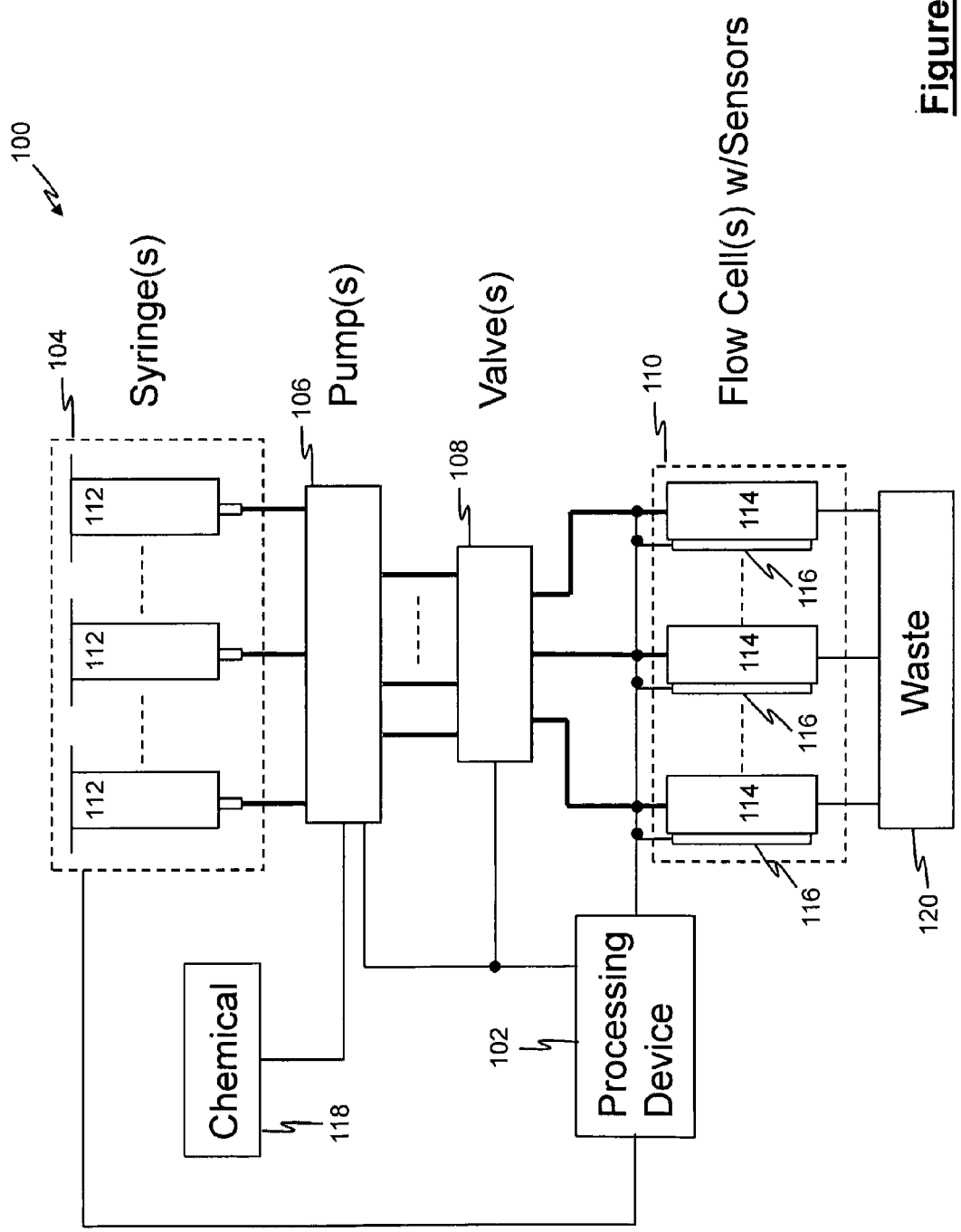
FIG. 4 is a schematic block diagram of the system in FIG. 1 illustrating one embodiment of an operational flow of specimen through the system.
Figure 5:
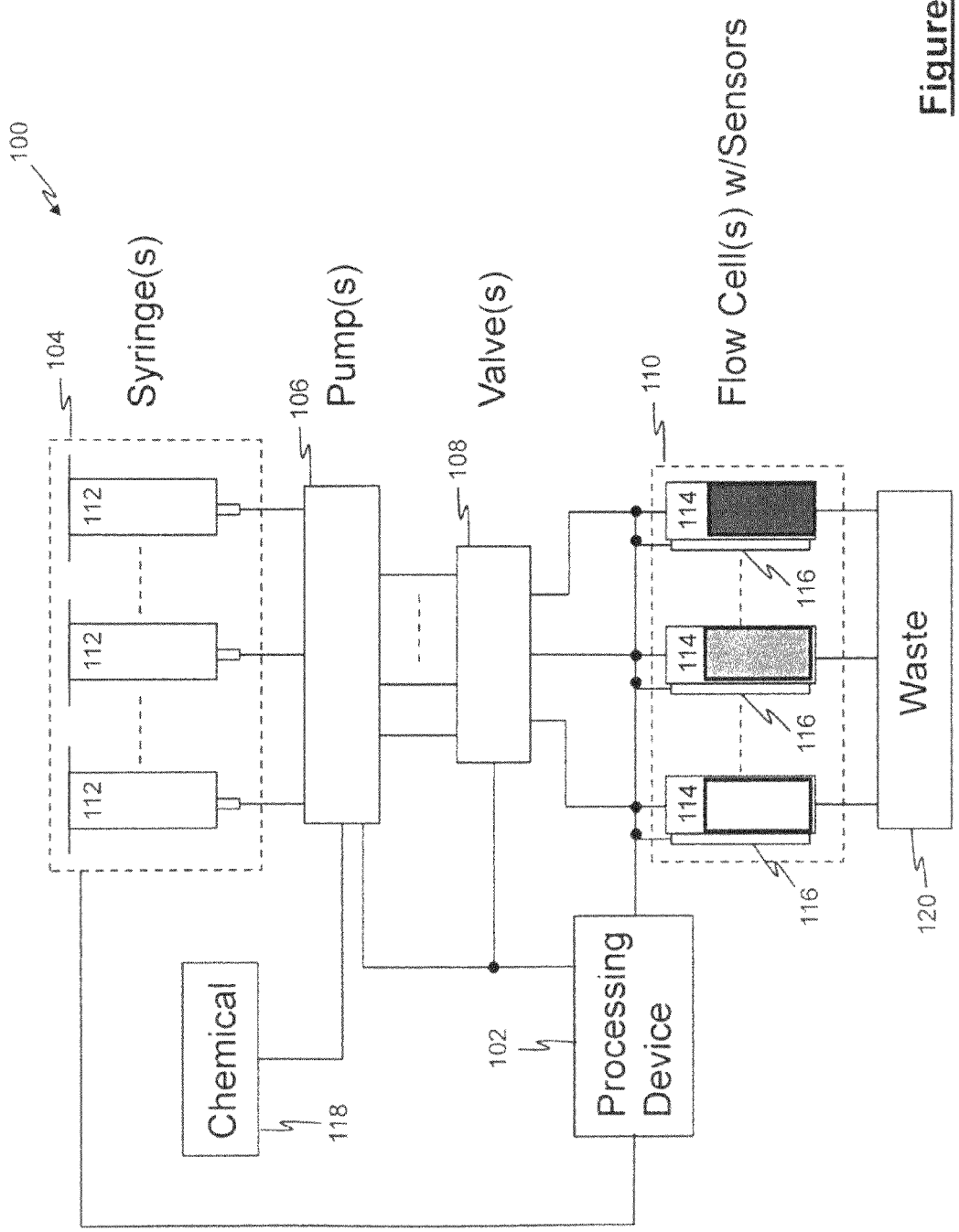
FIG. 5 is a schematic block diagram of the system in FIG. 1 illustrating one embodiment of an operational flow of specimen through the system.

Referring to FIG. 2, a block diagram illustrating a method 200 for implementing the system 100 for analyzing at least one biological sample is shown, in accordance with the present invention. The method 200 includes placing a specimen to be analyzed into at least one of the specimen input devices 104, as illustrated in FIG. 3 and shown in operational block 202. The specimen is then loaded into the system 100 for analysis, as illustrated in FIG. 4 and shown in operational block 204. This may be accomplished via a number of ways. For example, as illustrated in FIG. 5, one embodiment might include a plunger engagement device which is controlled by the processing device 102 to compress the plungers of each of the specimen input devices 104 (singly or together) to cause the specimen contained therein to flow into the pumping device 106. The flow valves 108 may then be operated to direct the specimen to the proper flow cell 110, as shown in operational block 206. A second embodiment might include the pumping device 106 being operated to draw the specimen (for example via a vacuum) from each of the specimen input devices 104 (singly or together). As above, the flow valves 108 may then be operated to direct the specimen to the proper flow cell 110.

As discussed hereinabove, the specimen is flowingly directed by the one or more of the flow valves 108 to one or more of the flow cells 110 for analysis. Once the specimen is disposed in its predetermined flow cell cavity 114, the plurality of sensors 116 are operated to sense at least one characteristic of the specimen, as shown in operational block 208. These characteristics may include, but not be limited to, pH, Nitrate Nitrogen, oxidation/reduction potential, conductivity/resistivity and/or refractometry. Other analyses may be performed as well, including but not limited to Chloride ions, Nitrite ions, Iodide ion, Calcium and surface tension. Essentially any measurements as desired may be conducted. For example any measurements helpful in determining and/or accessing the metabolic efficiency of the body at a cellular level may be conducted. Is should be appreciated that the system 100 may include specialized circuitry (internal or external) to control the flow valves 106, control the sensor devices 116 and/or to interpret the results of the analysis.

The results from the analysis conducted by sensors 116 are transmitted to processing device 102 for further analysis and/or processing. For example, the data may be translated into ASCII data for storage and interpretation by software, where the software may evaluate the data and present the data in a desired format (e.g. numerical and/or graphical "gauges") for a conceptual review. The data may also be evaluated according to at least one software algorithm to triangulate on what text recommendations to make to create a comprehensive report.

Figure 6:
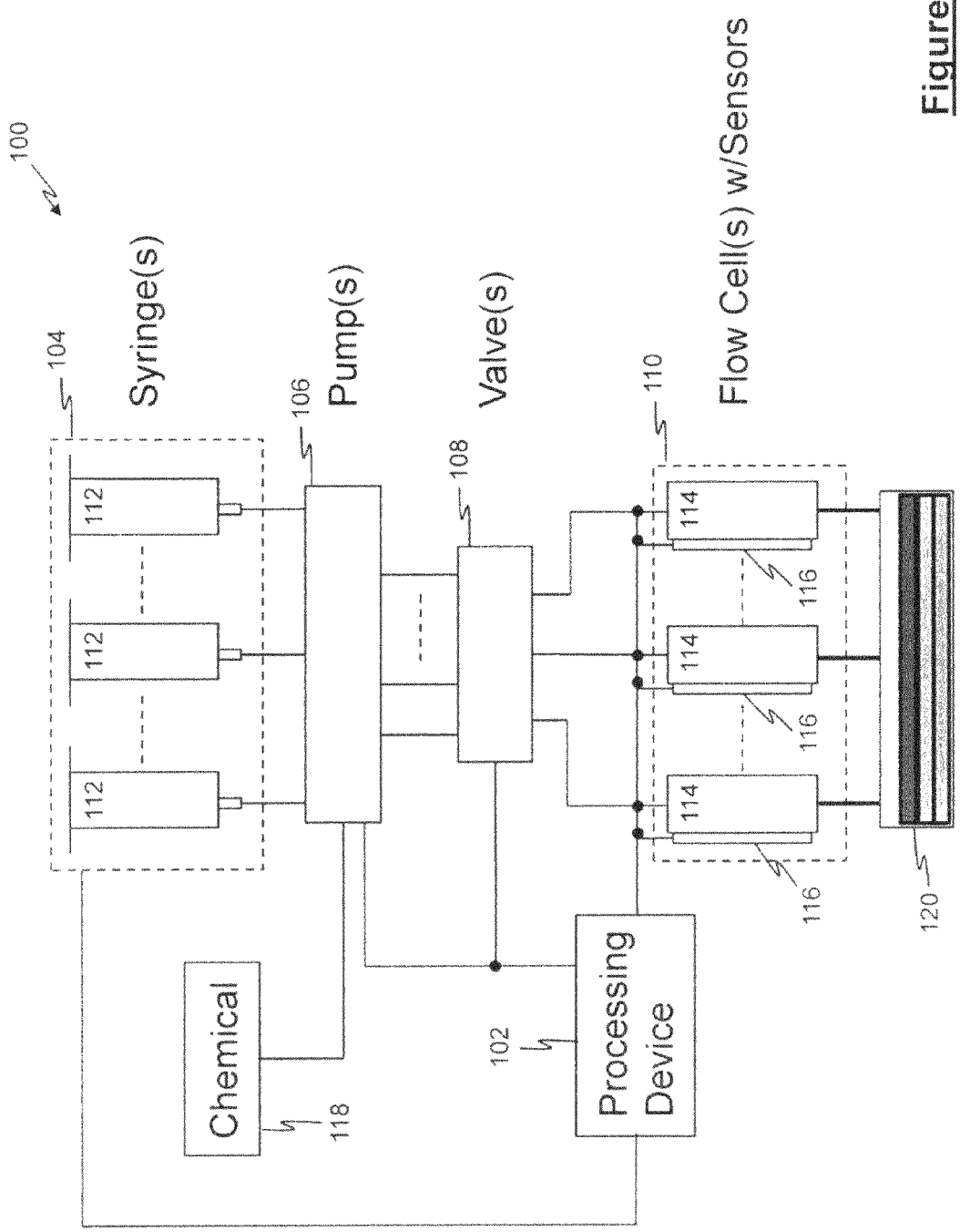
FIG. 6 is a schematic block diagram of the system in FIG. 1 illustrating one embodiment of an operational flow of specimen through the system.
Figure 7:
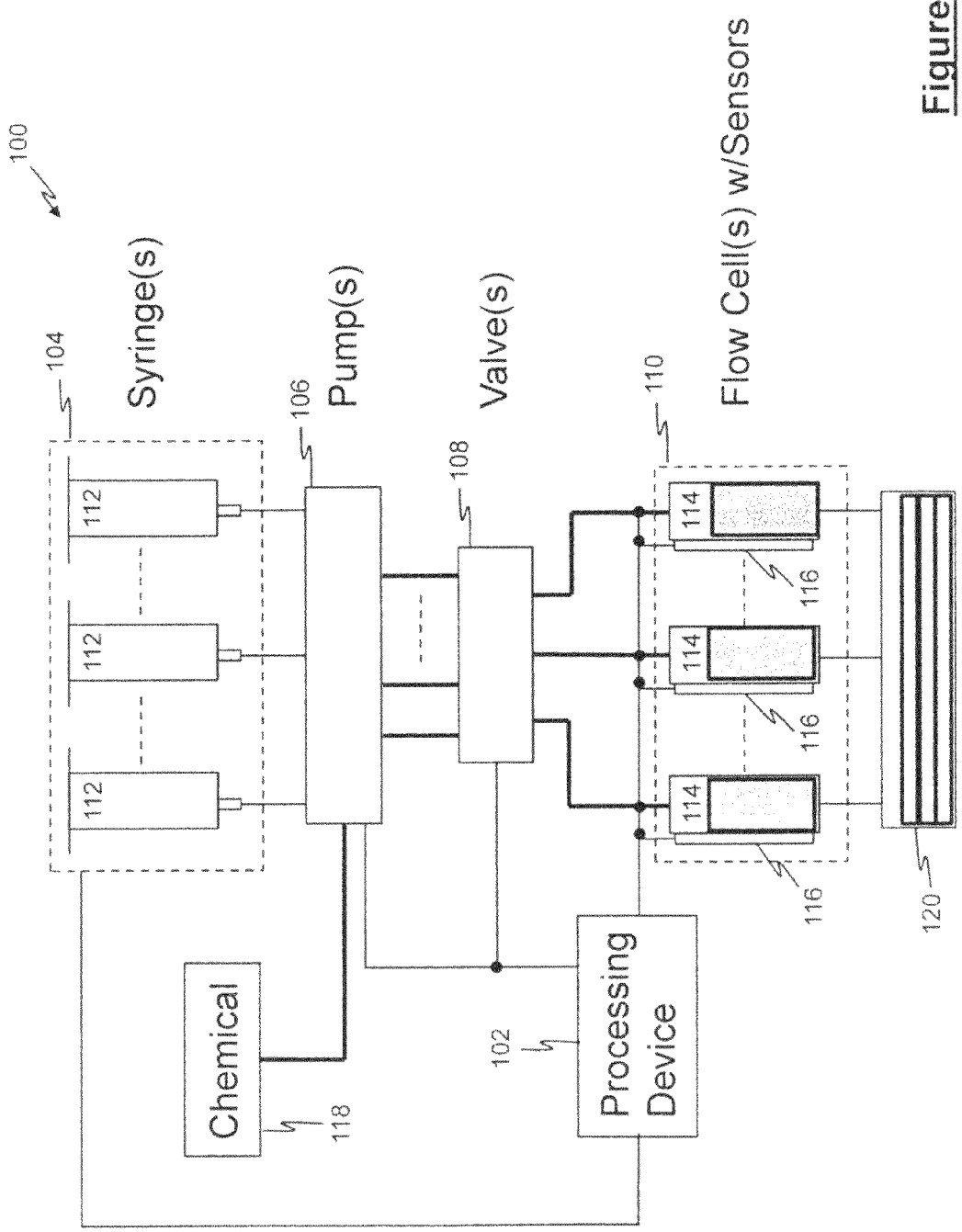
FIG. 7 is a schematic block diagram of the system in FIG. 1 illustrating one embodiment of an operational flow of specimen through the system.
Figure 21:
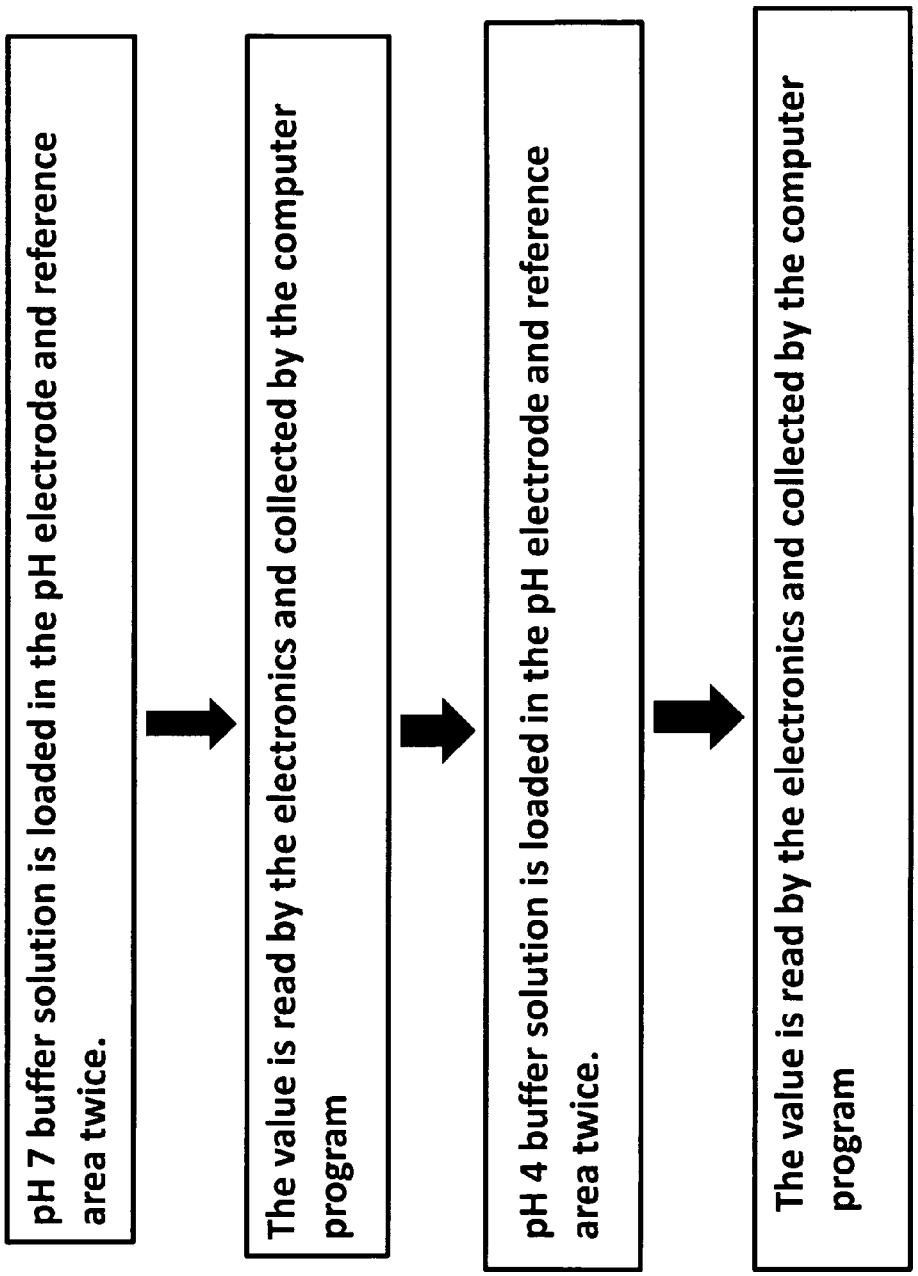
FIG. 21 is a general block diagram illustrating one embodiment of pH calibration in accordance with the invention.
Figure 22:
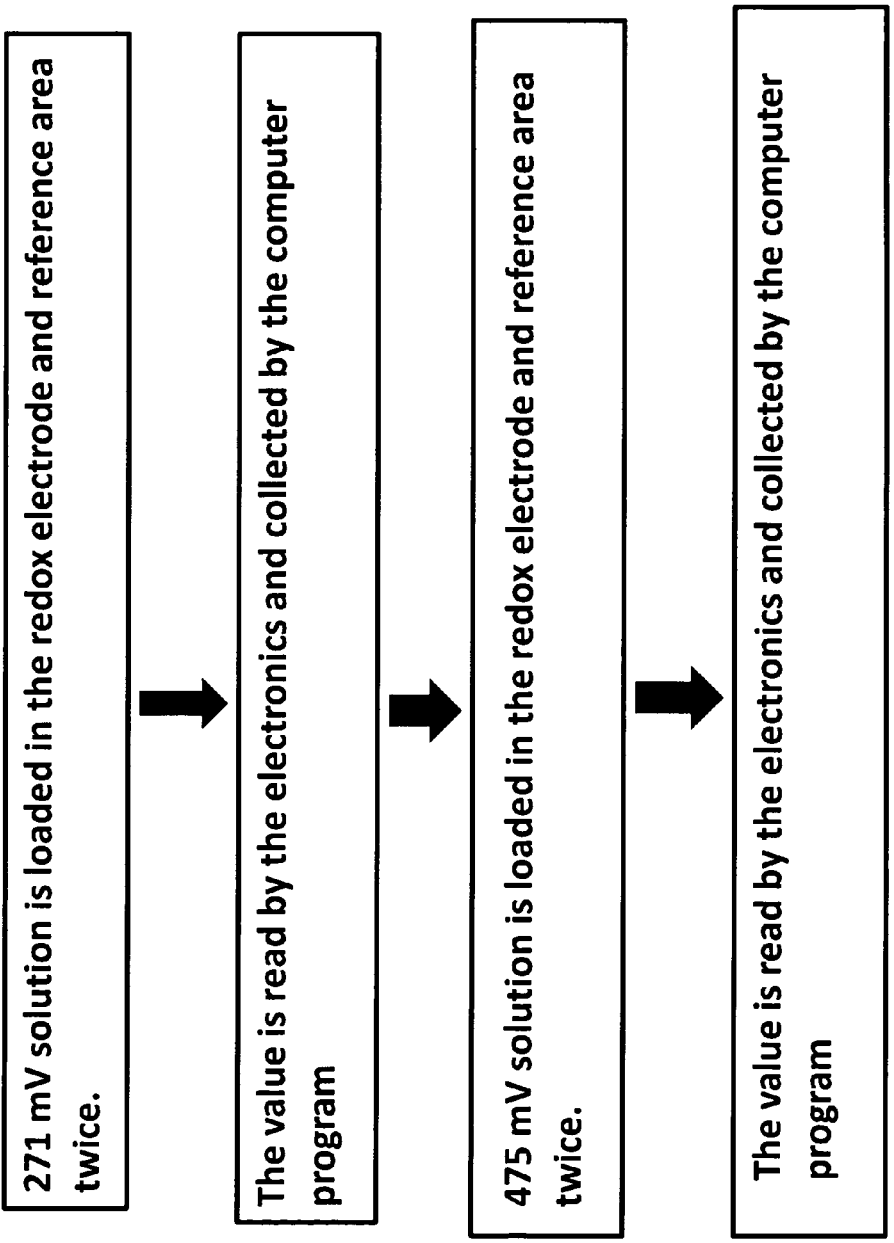
FIG. 22 is a general block diagram illustrating one embodiment of Redox calibration in accordance with the invention.
Figure 23:
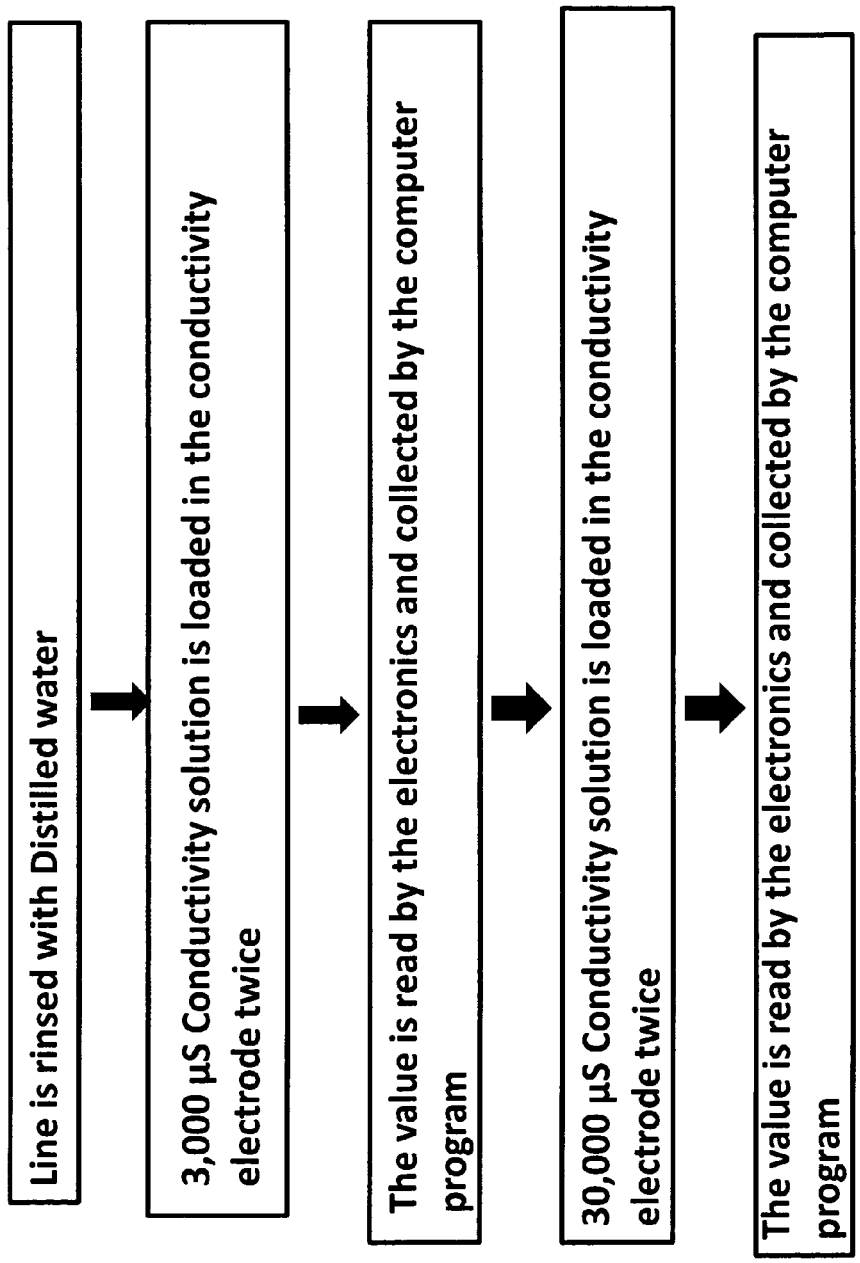
FIG. 23 is a general block diagram illustrating one embodiment of Conductivity/Resistivity calibration in accordance with the invention.

Once the analysis of the specimen(s) is complete, the specimen contained within the flow cell cavities 114 are then "flushed" into the waste container 120, as illustrated in FIG. 6 and as shown in operational block 210. The system 100 may then be 'cleaned' for future use by injecting a cleaning solution through the system 100, as shown in operational block 212. This may be accomplished by operating the pumping device 106 to cause the cleaning solution to flow out of the chemical reservoir 118 and through the system 100, as shown in FIG. 7. In accordance with one embodiment of the present invention, prior to calibration the system may be cleaned using distilled H2O and/or an enzyme solution suitable to the desired end purpose. The cleaning solution can then be flushed into the waste container 120.

In accordance with the present invention, flow cells may not be used. Rather the sensors may be disposed to contact the solution flowing within the flow path. One example as to how the system may function involves testing saliva and may include moving the substance to be tested (for example, saliva) from the syringe to the primary electrodes (i.e. sensors). These sensors read and store values indicative of pH, Redox (i.e. reduction) and/or conductivity/resistivity. The saliva is then moved to ion electrodes (i.e. sensors) where the sensors read and store values indicative of Nitrate, Nitrite and/or iodide levels. The saliva is then removed to the waste container and the system (line, syringe port) is rinsed with distilled water and/or an enzyme cleaning solution. Another example involves testing urine and may include moving the substance to be tested (for example, urine) from the syringe to the primary pH, Redox and conductivity/resistivity electrodes (i.e. sensors). These sensors read and store values indicative of pH, Redox (i.e. reduction) and/or conductivity/resistivity. The urine is then moved to ion electrodes (i.e. sensors) where the sensors read and store values indicative of Nitrate, Nitrite, Chloride, Iodide, Calcium and/or ammonium levels. The urine is then moved to the refractometer, where the refractive index, specific gravity and simple and/or complex sugars are measured. The urine is then removed to the waste container and the system (line, syringe port) is rinsed with distilled water and/or an enzyme cleaning solution.

The obtained data is then examined and analyzed responsive to predetermined values.

In accordance with the present invention, Acid/alkaline balance or buffer depletion may be determined by evaluating saliva and/or urine pH values. For example, if saliva pH is between 6.5 and 6.75 inclusive and urine pH is between 6.5 and 6.8 inclusive, then Acid/alkaline balance and/or buffer depletion may be considered optimal, whereas other value combinations may be indicative of early alkaline reserve use, late alkaline reserve use, early alkaline reserve loss and/or late state alkaline reserve loss, as is shown in FIG. 8. Additionally, oxidative stress may be determined by recognizing that rH2 is a modified Nernst equation that factors pH and temperature into the reading of ORP (Oxidation Reduction Potential), as shown in FIG. 9. Furthermore, electrolytes may be evaluated via the resistivity of saliva, as shown in FIG. 10, and carbohydrate metabolism may be measured using the refractometer as shown in FIG. 11. Moreover, the protein intake may be measured (in parts per million ppm) of the ION Nitrate Nitrogen and the protein metabolism may be made more "granular" as shown in FIG. 12 and FIG. 13, where the Nitrate number and/or the Ammonium number is determined. The Nitrate number and the Ammonium number may be added together to get a Total Urea number which may then be gauged to be positive or negative.

In accordance with the present invention, cell respiration and hydration may be determined, where cell respiration may be based on the saliva pH, wherein optimal values are typically centered on 6.4 pH as shown in FIG. 14, and hydration may be based on the refractometry of the urine, as shown in FIG. 15. Furthermore, liver stress/toxicity may be determined as shown in FIG. 16, Kidney stress may be determined as shown in FIG. 17, adrenal stress may be determined as shown in FIG. 18, anabolic/catabolic values may be determined as shown in FIG. 19 and inflammation may be determined as shown in FIG. 20. It should be appreciated that the values and approaches discussed hereinabove with regards to FIGS. 8-20 illustrate only one embodiment and may be modified for particular situations and desired results consistent with other embodiments that fall within the scope of the invention. It should be appreciated that each (or selected) parameter having a percentage score may be tallied and a percentage may be given as an overall health score.

In accordance with the present invention, calibration may be conducted (in addition to or separately) and are generally illustrated in FIGS. 21-25. These approaches include pH calibration (See FIG. 21), Redox Calibration (See FIG. 22), Conductivity/Resistivity Calibration (See FIG. 23), ION Calibration (See FIG. 24) and Refractometer Calibration (See FIG. 25).

It is contemplated that the system may be calibrated using a two (2) point calibration method. It should be appreciated that the system may be calibrated one or more times prior to and/or following each use. In accordance with one embodiment of the present invention, the system may be calibrated as follows. It should be appreciated that the calibration procedure is discussed in no particular order and may be conducted in any order desired. Additionally, although the calibration procedure is discussed in terms of a complete system calibration, all or only a portion of the system may be calibrated as desired. For ease in explanation, references made to 'flow path' include the actual flow tube and flow cell. First, a cleaning cycle is conducted by passing distilled $H_2O$ and/or an appropriate enzyme solution through the flow path for each of the sensing devices to remove any residue that may be present from previously tested or stored material. For example, the pH flow path is stored using a solution having a pH of 4. So this residue must be removed prior to calibration to achieve a correct calibration.

Calibration of the pH sensor may include several cycles of prewash (number of cycles is as desired suitable to the desired end purpose), i.e. flushing the pH flow path with a solution. In this case six (6) prewash cycles of the pH flow path are conducted (volume and acidity of solution is as desired suitable to the desired end purpose) with the first cycle using a solution having a pH=7, the second cycle using a solution having a pH=4, the third cycle using a solution having a pH=7, the fourth cycle using a solution having a pH=4, the fifth cycle using a solution having a pH=7 and the sixth cycle using a solution having a pH=4. At this point, 1 cc (volume and acidity of solution is as desired suitable to the desired end purpose) of solution having a pH=4 is then injected into and held within the pH flow path. The pH sensor is allowed to stabilize until a first stable pH=4 reading is achieved and recorded. 3 cc's (volume and acidity of solution is as desired suitable to the desired end purpose) of solution having a pH=4 is then injected into and held within the pH flow path. The pH sensor is allowed to stabilize until a second stable pH=4 reading is achieved and recorded. These are the first set of pH calibration reading points. A second calibration reading cycle is obtained by repeating the above discussed prewash cycle and introducing 1 cc (volume and acidity of solution is as desired suitable to the desired end purpose) of solution having a pH=7 into the pH flow path where the solution is held within the pH flow path until the pH sensor stabilizes. Once the pH sensor is stabilized, a first pH=7 calibration reading point is recorded. 3 cc's (volume and acidity of solution is as desired suitable to the desired end purpose) of solution having a pH=7 is then injected into and held within the pH flow path. The pH sensor is allowed to stabilize until a second stable pH=7 reading is achieved and recorded. These are the second set of pH calibration reading points.

Once the pH calibration readings have been obtained, the oxidation probe is calibrated by introducing into the oxidation probe flow path solutions with known values and recording the oxidation sensor readings. Although the invention is discussed as no flushing being conducted between the pH calibration and the oxidation calibration phases, flushing may be conducted as desired. In this embodiment, 1 cc (volume and electrical characteristic of solution is as desired suitable to the desired end purpose) of solution having a 271 mV charge is then injected into and held within the oxidation flow path. The oxidation sensor is allowed to stabilize until a stable reading is achieved. This is the first 271 mV oxidation calibration reading point. 3 cc's (volume and electrical characteristic of solution is as desired suitable to the desired end purpose) of solution having a 271 mV charge is then injected into and held within the oxidation flow path. The oxidation sensor is again allowed to stabilize until a stable reading is achieved. This is the second 271 mV oxidation calibration reading point. These are the first set of oxidation calibration reading points.

A second set of oxidation calibration reading points are obtained by introducing 1 cc (volume and electrical characteristic of solution is as desired suitable to the desired end purpose) of solution having a 475 mV charge into the oxidation flow path and holding the solution within the oxidation flow path. The oxidation sensor is allowed to stabilize until a stable reading is achieved. This is the first 475 mV oxidation calibration reading point. 3 cc's (volume and electrical characteristic of solution is as desired suitable to the desired end purpose) of solution having a 475 mV charge is then injected into and held within the oxidation flow path. The oxidation sensor is again allowed to stabilize until a stable reading is achieved. This is the second 475 mV oxidation calibration reading point. These are the second set of oxidation calibration reading points.

Once the oxidation calibration readings have been obtained, the system is flushed using an Iodine solution (volume as desired, for example 5 cc's). At this point, 1 cc (volume and conductivity of solution is as desired suitable to the desired end purpose) of solution having a conductivity=3 k siemens is then injected into and held within the conductivity flow path. The conductivity sensor is allowed to stabilize until a stable conductivity reading is achieved. This is the first 3 k siemens conductivity calibration reading point. 3 cc's (volume and conductivity of solution is as desired suitable to the desired end purpose) of solution having a conductivity=3 k siemens is then injected into and held within the conductivity flow path. The conductivity sensor is allowed to stabilize until a stable conductivity reading is achieved. This is the second 3 k siemens conductivity calibration reading point. These are the first set of conductivity calibration reading points. A second set of conductivity calibration reading points is obtained by repeating the above with a solution having 30 k siemens conductivity. Following the calibration of the conductivity flow sensor, the system is flushed using distilled $H_2O$ (volume as desired, for example 5 cc's), wherein approximately 5 cc's of distilled $H_2O$ is 'parked' in the conductivity probe.

Calibration of the ammonium and nitrate (AN) sensor is achieved by first introducing 1 cc (volume of solution is as desired suitable to the desired end purpose) of solution having 100 ppm of ammonium nitrogen and 100 ppm of nitrate nitrogen into the AN flow path as a pre-wash. At this point, 3 cc's (volume of solution is as desired suitable to the desired end purpose) of solution having 100 ppm of ammonium nitrogen and 100 ppm of nitrate nitrogen is introduced into the AN flow path and held within the AN flow path. The AN sensor is allowed to stabilize until a stable AN reading is achieved. This is the 100 ppm AN calibration reading point. A second calibration reading point is then obtained by introducing 3 cc's (volume of solution is as desired suitable to the desired end purpose) of solution having 1000 ppm of ammonium nitrogen and 1000 ppm of nitrate nitrogen into the AN flow path and holding the solution within the AN flow path until a stable AN reading is achieved. This is the 1000 ppm AN calibration reading point.

The AN sensor is then flushed with approximately 5 cc's of distilled $H_2O$ and the refractometer sensor is then disposed in approximately 5 cc's of distilled $H_2O$. Using a reference=0, if the refractometer sensor reading is 0 then the refractometer is determined to be good. However, if the refractometer sensor reading is 1 then the refractometer is determined to be bad.

In accordance with one embodiment of the present invention, the obtained results may be evaluated as shown and discussed herein. These results may be evaluated in whole or in part using at least one processing device programmed to implement the procedure as disclosed herein. In accordance with the invention, references may be based on general or specific conditions as desired, such as peak health of an ideal human group as opposed to two (2) standard deviations of the general population. It should be appreciated that the invention incorporates a synergistic approach and "looks" across all (or some) variables on an "energy in" "energy out" basis. By examining values on an "energy in" "energy out" basis at the cellular level the invention evaluates proteins & carbohydrates, metabolism efficiency, oxygen transport, rate of aging, waste etc. . . . to achieve a situation (condition and/or treatment approach) where the body is maximizing energy and minimizing wear, toxic overload and body function breakdown. Accordingly, based on results achieved using the present invention, lifestyle, exercise, health and nutritional recommendations can be made.

It should be appreciated that a personal computer may be provided to allow a user to control the functions of the system 100 via a Graphical User Interface. It should also be appreciated that the processing device 102 may control all or some of the components of the system 100 (such as the specimen input devices 104, the pumping device 106, the flow valves 108, the flow cells 110, the sensors 116 and the solution reservoir 118.

While the invention has been described with reference to an exemplary embodiment, it will be understood by those skilled in the art that various changes, omissions and/or additions may be made and equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

In accordance with the present invention, it is contemplated that multiple measurements may be made by each of the sensors in a manner responsive to a desired end result. It is further contemplated that obtained and/or processed data may be displayed via any display device suitable to the desired end purpose, such as a paper printout, a computer screen, a television, a plasma display and/or a Liquid Crystal Display (LCD). System 100 may be operated and/or monitored via a network connection, such as a wireless network (cellular, pager, RF), Local Area Network, Wide Area Network, Ethernet and/or Modem.

It is contemplated that the processing device may store obtained and/or processed data and measurement results in a data storage device and/or a volatile memory of the processing device (e.g. RAM) and/or on a persistent storage device. It should also be noted that data may be stored in a volatile and/or a non-volatile memory location which may be disposed in any location suitable to the desired end purpose, such as a remote server. In addition, the data storage device may be used to store individual test data and/or group test data which may be specific to a desired purpose, such as data for a specific patient and/or test, wherein the data may include a large range of information, such as patient specific data and/or patient history data.

In accordance with an exemplary embodiment, system 100 may advantageously be self-calibrating and automated for evaluating multiple samples. Moreover, although system 100 discloses contact sensors as its sensing devices, it is contemplated that any sensing device and/or method may be implemented using system 100, for example optical sensors. A machine-readable computer program code and/or a medium encoded with a machine-readable computer program code for measuring the characteristics of samples and processing the measured data using system 100, the code and/or medium including instructions for causing a controller to implement a method including operating system 100 is contemplated.

In accordance with an exemplary embodiment, the processing may be implemented by a controller disposed internal, external or internally and externally to system 100. In addition, processing of samples may be implemented through a controller operating in response to a computer program. In order to perform the prescribed functions and desired processing, as well as the computations therefore (e.g. execution control algorithm(s), the control processes prescribed herein, and the like), the controller may includes, but not be limited to, a processor(s), computer(s), memory, storage, register(s), timing, interrupt(s), communication interface(s), and input/output signal interface(s), as well as combination comprising at least one of the foregoing.

The invention may be embodied in the form of a computer or controller implemented processes. The invention may also be embodied in the form of computer program code containing instructions embodied in tangible media, such as floppy diskettes, CD-ROMs, hard drives, and/or any other computer-readable medium, wherein when the computer program code is loaded into and executed by a computer or controller, the computer or controller becomes an apparatus for practicing the invention. The invention can also be embodied in the form of computer program code, for example, whether stored in a storage medium, loaded into and/or executed by a computer or controller, or transmitted over some transmission medium, such as over electrical wiring or cabling, through fiber optics, or via electromagnetic radiation, wherein when the computer program code is loaded into and executed by a computer or a controller, the computer or controller becomes an apparatus for practicing the invention. When implemented on a general-purpose microprocessor the computer program code segments may configure the microprocessor to create specific logic circuits.

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment disclosed as the best mode contemplated for carrying out this invention.

What is claimed is:

1. A device for analyzing a biological specimen from a human subject, the device comprising:
    a specimen input device for receiving a specimen from the human subject;
    a pumping device in flow communication with a chemical reservoir and said specimen input device; and
    a flow cell device in flow communication with said pumping device via a flow valve device, wherein said flow cell device is configured to contain said specimen and includes a pH sensing device, an oxidation sensing device, a conductivity sensing device, an ammonium and nitrate sensing device and a refractometer sensing device configured to sense characteristics of the specimen responsive to the pH, oxidation, conductivity, ammonium content, nitrate content and refractomety of said specimen.

2. The device of claim 1, further comprising at least one processing device configured to receive said characteristics of the specimen, wherein said at least one processing device examines said characteristics to evaluate pH level, oxidative stress, electrolyte level, carbohydrate metabolism, protein metabolism, cell respiration, hydration liver stress/toxicity, kidney stress, adrenal stress, anabolic/catabolic level and inflammation level of the human subject.

3. The device of claim 1, wherein said specimen input device includes at least one specimen input container.

4. The device of claim 1, wherein said specimen input device includes a plurality of specimen input containers.

5. The device of claim 1, wherein said flow cell device includes at least one flow cell container.

6. The device of claim 1, wherein said flow cell device includes a plurality of flow cell containers.

7. The device of claim 1, wherein said specimen input device includes a plurality of specimen input containers, said flow cell device includes a plurality of flow cell containers and wherein said pumping device is configurable to communicate each of said specimen input containers to at least one of said flow cell containers.

8. The device of claim 1, further comprising a waste container, wherein said waste container is in flow communication with said flow cell device.

9. The device of claim 1, wherein said chemical reservoir is in flow communication with said valve device and said flow cell device via said pumping device.

* * * * *